US008961933B2

(12) United States Patent
Reineri et al.

(10) Patent No.: US 8,961,933 B2
(45) Date of Patent: Feb. 24, 2015

(54) PROCESS FOR THE PREPARATION OF AQUEOUS SOLUTIONS OF HYPERPOLARIZED MOLECULES

(75) Inventors: Francesca Reineri, Cuneo (IT); Alessandra Viale, Turin (IT); Giovanni Battista Giovenzana, Novara (IT); Daniela Santelia, Caselle Torinese (IT); Walter Dastru', Turin (IT); Roberto Gobetto, Gassino Torinese (IT); Silvio Aime, Carignano (IT); Fulvio Uggeri, Codogno (IT)

(73) Assignee: Bracco Imaging S.p.A., Milan (IT)

( * ) Notice: Subject to any disclaimer, the term of this patent is extended or adjusted under 35 U.S.C. 154(b) by 564 days.

(21) Appl. No.: 13/122,209

(22) PCT Filed: Sep. 30, 2009

(86) PCT No.: PCT/EP2009/062674
§ 371 (c)(1),
(2), (4) Date: Apr. 1, 2011

(87) PCT Pub. No.: WO2010/037771
PCT Pub. Date: Apr. 8, 2010

(65) Prior Publication Data
US 2011/0178393 A1 Jul. 21, 2011

(30) Foreign Application Priority Data

Oct. 3, 2008 (IT) .............................. MI2008A1765
May 28, 2009 (IT) .............................. MI2009A0942

(51) Int. Cl.
A61B 5/055 (2006.01)
A61K 49/10 (2006.01)
A61K 49/00 (2006.01)

(52) U.S. Cl.
CPC ..................................... A61K 49/10 (2013.01)
USPC .......................................... 424/9.1; 424/9.3

(58) Field of Classification Search
USPC .......................................................... 424/9.3
See application file for complete search history.

(56) References Cited

U.S. PATENT DOCUMENTS

| 3,615,723 | A | | 10/1971 | Meade |
| 5,334,791 | A | * | 8/1994 | Cavell et al. ................... 585/277 |
| 6,574,495 | B1 | | 6/2003 | Golman et al. |
| 6,872,380 | B2 | * | 3/2005 | Axelsson et al. ............... 424/9.3 |
| 2011/0095759 | A1 | * | 4/2011 | Bhattacharya et al. ........ 324/307 |

FOREIGN PATENT DOCUMENTS

| CN | 1306441 A | 8/2001 |
| EP | 1548454 A1 | 6/2006 |
| JP | 2000-513979 A | 10/2000 |
| JP | 2001-522819 A | 11/2001 |
| JP | 2003-500369 A | 1/2003 |
| WO | 98-01766 A | 1/1998 |
| WO | 98-01766 A1 | 1/1998 |
| WO | 99/24080 A | 5/1999 |
| WO | 2007/044867 A | 4/2007 |

OTHER PUBLICATIONS

Eisenberg et al. (Adv. Chem. 1992, 230, 47-74).*
Jonischkeit et al. (J. Chem. Phys. 2006, 124, 201109-1 to 201109-5).*
Koptyug et al. (J. Am. Chem. Soc. 2007, 5580-5586).*
Aime, S. et al., "Para-Hydrogenation of unsaturated moieties on poly(lysine) derived substrates for teh development of novel hyperpolarized MRI contrast agents", Organic and Biomolecular Chemistry, vol. 3, No. 21, Nov. 7, 2005, pp. 3948-3954, XP002538146.
Goldman, M. et al., "Design and implementation of 13C hyper polarization from para-hydrogen, for new MRI contrast agents", Comptes Rendus-Chimie, Elsevier, Paris, FR, vol. 9, No. 3-4, Mar. 1, 2006, pp. 357-363, XP024979705, ISSN: 1631-0748.
Goldman, M. et al., "Hyperpolarization of 13C thruogh order transfer from parahydrogen: A new contrast agent for MRI", Magnetic Resonance Imaging, Elsevier Science, Tarrytown, NY, US, vol. 23, No. 2, Feb. 1, 2005, pp. 153-157, XP004843472, ISSN: 0730-725X.
Golman, K. et al., "Molecular imaging using hyperpolarized 13C", The British Journal of Radiology 2003, vol. 76 Spec. No. 2, 2003, pp. S118-S127, XP002538147, ISSN: 0007-1285.
Hovener, J-B. et al., "Pasadena hyperpolarization of 13C biomolecules: equipment design and installation", Magnetic Resonance Materials in Physics, Biology and Medicine 200904 DE, vol. 22, No. 2, Apr. 2009, pp. 111-121, XP002538149, ISSN: 0968-5243.
Joo, F., "Aqueous biphasic hydrogenations", Accounts of Chemical Research Sep. 2002, vol. 35, No. 9, Sep. 2002, pp. 738-745, XP002538144, ISSN: 0001-4842.
Reineri, F. et al., "New hyperpolarized contrast agents for 13C-MRI from para-hydrogenation of oligooxyethylenic alkynes", Journal of the American Chemical Society 20081112 American Chemical Society US, vol. 130, No. 45, Nov. 12, 2008, pp. 15047-15053, XP002538148.
Wang, C. et al., "Broader, greener, and more efficient: recent advances in asymmetric transfer hydrogenation", Chemistry, An Asian Journal Oct. 6, 2008, vol. 3, No. 10, 08-27-208, pp. 1750-1770, XP002538145, ISSN: 1861-471X.
PCT International Search Report for PCT/EP2009/062674, mail date Mar. 2, 2010.
PCT Written Opinion of the International Searching Authority for PCT/EP2009/062674, mail date Mar. 2, 2010.
Chinese Office Action, application No. 200980138851.X, mail date Apr. 27, 2012 (English translation).

(Continued)

Primary Examiner — Michael G Hartley
Assistant Examiner — Melissa Perreira
(74) Attorney, Agent, or Firm — M. Caragh Noone

(57) ABSTRACT

The invention relates to a one-step process for the preparation of aqueous solutions of hyperpolarized molecules in which, in a single step, the said hyperpolarized molecules are separated from the crude solution by means of a fast phase-transfer extraction and isolated in an impurity-free aqueous solution, ready for use in the MRI diagnostic imaging of organs, region or tissues of the human or animal body.

14 Claims, 5 Drawing Sheets

(56) References Cited

OTHER PUBLICATIONS

Chinese Office Action, application No. 200980138851.X, mail date Nov. 9, 2012 (English translation).

Chinese Office Action, application No. 200980138851.X, mail date Jul. 23, 2013 (English translation).

Israel Office Action, application No. 212117, mail date Jan. 27, 2014 (English translation provided by Israel agent).

European Office Action, application No. 09783592.0, mail date Feb. 24, 2014.

Altes, Talissa A. et al., "Hyperpolarized Gas MR Imaging of the Lung", Symposium, J. Thorac Imaging, 2004, vol. 19, No. 4, pp. 250-258, Lippincott Williams & Wilkins.

Bargon, J. et al., "Parahydrogen-Induced Hyperpolarization of 15N", Proc. Intl. Soc. Mag. Reson. Med., 2007, vol. 15, p. 1317.

Bowers, Clifford R., "Sensitivity Enhancement Utilizing Parahydrogen", Encyclopedia of nuclear magnetic resonance, 2002, vol. 9, Wiley, Chichester, New York, ISBN: 0471490822, pp. 750-770.

Goldman, Maurice et al., "Conversion of a proton pair para order into 13C polarization by rf irradiation, for use in MRI", Comptes Rendus PHYSIQUE, 2005, vol. 6, pp. 575-581, Elsevier SAS.

Golman, K. et al., "Parahydrogen-Induced Polarization in Imaging: Subsecond 13C Angiography", Magnetic Resonance in Medicine, Wiley-Liss, Inc., 2001, vol. 46, pp. 1-5.

Grant, A.K. et al, "Early Experience with Simple Methods for Parahydrogen-Induced Hyperpolarization", : Proc. Intl. Soc. Mag. Reson. Med., 2006, v14, pg. 2552.

Johannesson, Haukur et al., "Transfer of para-hydrogen spin order into polarization of diabatic field cycling: highly polarized nuclear spin systems and dipolar interations in NMR", Comptes Rendus PHYSIQUE, 2004, vol. 5, pp. 315-324, Elsevier SAS.

Kohler, S.J. et al., "In Vivo 13Carbon Metabolic Imaging at 3T With Hyperpolarized 13C-1-Pyruvate", Magnetic Resonance in Medicine, 2007, vol. 58, pp. 65-69, Wiley-Liss, Inc.

Mansson, Sven et al., "13C imaging—a new diagnostic platform", Eur Radiol, 2006, vol. 16, pp. 57-67, doi: 10.1007/s00330-005-2806-x, Springer-Verlag.

Nelson, S.J. et al., "DNP-Hyperpolarized 13C Magnetic Resonance Metabolic Imaging for Cancer Applications", Appl Magn Reson: Author Manuscript, 2008, vol. 34, No. 3-4, pp. 533-544, doi:10.1007/s00723-008-0136-2, NIH Public Access Author Manuscript.

Oros, Ana-Maria et al., "Hyperpolarized xenon in NMR and MRI", Phys. Med. Biol., 2004, vol. 49, pp. R105-R153, Institute of Physics Publishing Ltd, doi:10.1088/0031-9155/49/20/R01.

Office Action: Notification of Reasons for Refusal, for Japanese application No. 2011-529542, mail date Oct. 8, 2013 [B0634 JP00].

\* cited by examiner

PROCESS FOR THE PREPARATION OF AQUEOUS SOLUTIONS OF HYPERPOLARIZED MOLECULES

CROSS-REFERENCE TO RELATED APPLICATIONS

This application is the national stage application of corresponding international application number PCT/EP2009/062674 filed Sep. 30, 2009, which claims priority to and the benefit of Italian application nos. MI2008A001765, filed Oct. 3, 2008; and MI2009A000942, filed May 28, 2009, all of which are hereby incorporated by reference.

TECHNICAL FIELD

The present invention relates to the field of Magnetic Resonance Imaging (MRI). More particularly, the invention relates to a process for the preparation of aqueous solutions of hyperpolarized molecules ready for use in in vivo MRI diagnostic imaging, thereof use in the preparation of MRI contrast agent, and an investigation method in which the said aqueous solutions are directly employed for producing diagnostic MR images of a human or non-human animal body organ, region or tissue.

BACKGROUND

Magnetic Resonance Imaging is a well established powerful tool for medical and biological investigations both in vitro and in vivo. The main drawback of this technique is due to the intrinsic low sensitivity of the NMR spectroscopy on which MRI is based. In fact, the intensity of NMR signals depends on the difference between the nuclear spin states populations of the imaging nuclei. According to the well known Boltzman equation ($\Delta N = \gamma h B_0/(2\pi kT)$), this difference is a function of temperature and applied magnetic field, and, at thermal equilibrium, it is in the order of $10^{-5}$, i.e. very low.

The use of hyperpolarized molecules has been recently proposed as a possible solution of the said drawback and, in recent years, many efforts have been devoted to the development of both feasible and effective MR-hyperpolarization procedures.

In this regard, the most straightforward is the so called "brute force" method, that consists in keeping the molecule of interest at high magnetic field strength (up to 20 T) and low temperature, close to absolute zero, for a given period of time. This method is of general applicability, but it requires the application of an appropriate "relaxation switch" that consents to quickly promote the nuclear transitions needed to create nuclear polarization, and that must be removed or, otherwise, "turned off" immediately after the trial. However, as a "relaxation switch" fit for such a purpose has not already been found, this approach is not, at now, exploitable.

A second method is the so-called "optical pumping/spin exchange", which can be applied to noble gases such as $^{129}$Xe and $^{3}$He. In this case a circularly polarized laser beam is used to irradiate a gaseous mixture of the selected gas and an alkaline metal vapour. This allows providing Xe and He with a high degrees of polarization that can be maintained for long time, thanks to the long relaxation times of these nuclei.

MRI studies of the respiratory system conducted with the use of hyperpolarized gases thus obtained are known. In this regard, see, for instance, J. Thoracic Imag. 2004, vol. 19, pp. 250-258; Phys. Med. Biol. 2004, vol. 49 pp. 105-R153. However, as formerly said, this technique is not of general applicability, but it is just limited to the polarization of noble gases.

The population difference between nuclear spin levels can also be increased through exploiting the "Overhauser" effect between the nucleus of interest and the unpaired electrons of coupled paramagnetic species, according to a technique known as Dynamic Nuclear Polarization or DNP. This technique has been used, for instance, to hyperpolarize some molecules of biological interest, including urea, pyruvate and metabolic derivatives thereof, currently exploited for studies of metabolic profiles performed by use of MRI (see, for instance, Europ. Radiol. 2006, vol. 16, pp. 57-67, Magn. Res. in Med., vol 58, 2007, pp. 65-69; Appl. Magn. Res. 2008, vol. 34, pp. 533-544).

Although this technique may be applied, at least in principle, to any type of molecule, the need for a powerful cryostat and a suitable "hardware" allowing the irradiation of electrons at low temperature constitutes, in fact, a limit to its more general use.

Further difficulties may also arise from the need for an efficient procedure allowing the rapid dissolution of the substrate after the hyperpolarization, and the separation of the highly toxic paramagnetic radical before the in vivo administration of the hyperpolarized substrate.

The alternative use of hyperpolarized molecules obtained by addition of para-hydrogen on unsaturated substrates by means of a procedure known as Para Hydrogen Induced Polarization (PHIP) has also been proposed, for instance, in U.S. Pat. No. 6,574,495.

The main advantage of this procedure relies on that it allows to obtain populations of the nuclear spin levels deeply altered compared with those determined by the Boltzmann thermodynamics without having to use extremely low temperatures and complex dissolution procedures such as those used in the DNP method. As such, it can be regarded as a simpler and cheaper alternative to the DNP hyperpolarization technique.

As said, the PHIP procedure relies on the catalytic hydrogenation of an unsaturated substrate, or MR agent precursor, with hydrogen gas enriched in the para isomer.

The hydrogen molecule, in fact, exists in two isomeric spin forms, namely ortho-hydrogen (o-$H_2$), and para-hydrogen (p-$H_2$). The ortho isomer, which is symmetric with respect to the exchange of the two protons, is triply degenerate (triplet state), while the para isomer, which is anti-symmetric, is a singlet state. Furthermore, the ortho isomer has spin equal to 1 (S=1) and is NMR active, while the para isomer, having spin equal to 0 (S=0), is NMR silent.

At room temperature the equilibrium mixture in which the two forms exist, otherwise called normal-hydrogen, contains 75% of ortho and 25% of para isomer, but, being the para state thermodynamically favoured and due to the relatively high rotational temperature of the $H_2$ molecule, it is possible to enrich the equilibrium mixture in the para isomer, by keeping it at low temperature.

For instance, at 77 K (liquid $N_2$ temperature) the two forms exist with a 52% (para): 48% (ortho) ratio and at 20 K the mixture is formed by 99.8% of the para isomer.

At normal conditions, the equilibration rate between the two isomers is very low, because it involves a singlet-triplet transition that is forbidden by selection rules. However, in the presence of a suitable catalyst, for instance selected from iron oxides such as $Fe_3O_4$, $Fe_2O_3$ and activated charcoal, the interconversion may be rapidly obtained (for example, in few hours). The para enrichment thus obtained can be then maintained at room temperature, provided that the conversion catalyst, and any other paramagnetic impurity, are totally removed. By this way it is possible to have a non-equilibrium mixture, i.e. a hydrogen mixture enriched in the para isomer, also called para-hydrogen, at room temperature, that remains stable for several hours.

Although NMR silent, when para-hydrogen is added to an unsaturated molecule, its symmetry can be broken with the formation of an AX spin system allowing to observe the hyper-polarization, or, in other words, a significantly intensified signal in the NMR spectrum of the para-hydrogenated compound that corresponds to the hyperpolarized proton nucleus. Typically, in $^1$H NMR spectra the sensitivity increase measured in terms of enhancement of the MR signal can be as high as a factor $10^5$ (see, for instance, Sensitivity enhancement utilizing parahydrogen, C. R. Bowers, Encyclopedia of NMR Vol. 9 2002 pp 750-770).

Nevertheless, a skilled practitioner is aware that, for in vivo MRI purposes, heteronuclear (non-proton) hyperpolarization is more useful than that, even so high, of protons. That is because, in in vivo conditions, the proton signal of a parahydrogenated contrast agent would overlap with endogenous $^1$H signals of tissue water. On the contrary, the almost total absence of endogenous signal for non-proton nuclei results in the practical absence of background noise, thus allowing for the registration of images with a high signal to noise ratio, where the contrast is only given by the difference in signal intensity between regions reached by the hyperpolarized molecule and the areas in which the same is absent.

Further benefits are due to longer $T_1$ values characterizing non-proton nuclei (which limit the polarization loss due to relaxation) and to the width of chemical shift range associated with the same, when included in different molecules, or, in other words, to the fact that the value of chemical shift associated with a given heteronucleus is different into different molecules, wherein this makes possible to view different molecules at one time.

The main interest is, therefore, directed to feasible and effective MR-procedures for the polarization of non-proton nuclei, especially of nuclei having nuclear spin=½ such as, for instance, $^{13}$C, $^{15}$N and $^{29}$Si, as well as to contrast agents comprising non-proton hyperpolarized nuclei, and, especially, $^{13}$C enriched hyperpolarized substances.

Interestingly, the PHIP hyperpolarization method allows to provide $^{13}$C and $^{15}$N hyperpolarized molecules in a simpler and cheaper way, especially when compared with the DNP technique.

For contrast, in order to obtain a $^{13}$C hyperpolarized molecule that is effective for use in in vivo MRI medical imaging, the following requirements must be satisfied:

i) The substrate molecule must be easily hydrogenable;
ii) The substrate molecule must contain a $^{13}$C carbon atom within a distance of three bonds from the protons added to the molecule with para-hydrogen;
iii) The molecular weight of the substrate molecule should be low, and preferably lower than 500 Da, in order to limit the relaxation rate;
iv) The hyperpolarization product must be water soluble and physiologically tolerable;
v) A parahydrogenation catalyst must be used allowing to promote the transfer of both protons from one $H_2$ molecule to the same substrate molecule, so that the spin correlation is maintained. Catalysts enabling this kind of transfer are the homogeneous ones, such as, for instance, Rh or Ir organometallic complexes that, due to their high toxicity, must be removed from the reaction mixture before injection;
vi) To be effective in MRI imaging, the spin-order of the para-hydrogen has to be transformed into $^{13}$C net magnetization.
vii) As aqueous solutions of the parahydrogenation product are used for in vivo applications, the hydrogenation reaction should be carried out directly in water or, alternatively, the organic solvent being used for hydrogenation must be totally removed.

It will be apparent to a skilled person that the same kind of criteria equally applies for the preparation of hyperpolarized substances suitably enriched with a non-proton nucleus different from $^{13}$C.

It stems from the above that the main problems one has to face when using PHIP hyperpolarization methods are due to the use of toxic hydrogenation catalysts and of organic solvents in which both the hydrogenation catalyst and hydrogen are more soluble, while, for contrast, for in vivo MRI applications physiologically acceptable aqueous solutions of the parahydrogenation products are needed.

Several kinds of hydrogenation catalysts based on transition metals are, therefore, under intense scrutiny.

Homogeneous transition metal based catalyst have shown to offer best activity and selectivity. In particular, catalysts that have shown to allow higher polarization on $^{13}$C after para-$H_2$ addition to unsaturated precursor are Rh(I) cationic complexes, preferably containing a chelating phosphine ligand, for example DPPB (diphenylphosphine butane) or DPPE (diphenylphosphine ethane), and a diene molecule such as, for instance, cyclooctadiene or norbornadiene (see, for instance, K. Goldman et al., Magn. Res. Med. 2001, 46 1-5)

The highest efficiency of these hydrogenation catalysts is achieved in organic solvents, preferably in acetone, in which they are more soluble. It is, however, clear that organic solvents must be totally removed from the reaction mixture before the same is formulated in an aqueous medium for the in vivo administration. This task can, for instance, be achieved by means of a "spray-drier" located immediately downstream of the reactor, through a process similar to that commonly used in pharmaceutical technology to transform a solution into solid dry particles (see, for instance, U.S. Pat. No. 3,615,723). In this case, the fluid material is sprayed into the drying chamber where it is nebulised and dispersed by a carrier gas; the more volatile solvent is then distilled by applying vacuum while water, previously added to the mixture, remains in the "drier" thus providing a water solution of the added material. However, as low molecular weight molecules (less than 500 Da) are preferably used as parahydrogenation substrates, a main drawback associated with the use of the above procedure stems from the possible loss of the hydrogenation product along with the organic solvent.

On the other side, aqueous solvents have also been used, for instance in WO99/24080, together with Rh(I) cationic complexes containing some ionic/polar groups, mainly on the phosphyne ligands, purposely introduced to improve the catalysts water solubility and, in turn, their efficiency in an aqueous medium.

However, an important drawback to be addressed when working in an aqueous medium is due to the low solubility of hydrogen in water that makes it necessary to operate at very high pressure (50-100 bar) or at lower pressure (10-15 bar) but under laminar flow conditions and into suitable reactors disclosed, for instance, in Magn. Res. Mater. Phys. 2009, 22, 111. In addition, the use of homogeneous catalyst is hampered by the difficulties of catalyst recovery and recycling with simultaneous isolation of a catalyst-free product solution.

A method typically used to remove cationic Rh complexes comprises, for example, percolating the reaction mixture on a suitable cation-exchange resin, although this procedure leads to a marked loss of polarization.

Catalysts based on Rh (I) supported on a solid surface, for instance silica or polymers, have, alternatively, been used. However, the net polarization obtainable with supported catalysts is significantly lower than that observed with homogeneous catalysts, probably because of the lower mobility of the substrate-catalyst adduct that results in an increased relaxation rate at intermediate level. Therefore, a need still remains for easy and cheap procedures able to overcome the above purification problems and to provide aqueous solutions of hyperpolarized molecules ready for use in MR imaging of a human or non-human animal body.

DESCRIPTION OF THE INVENTION

The solution offered by the present invention relates to an improved procedure for the one-step production and rapid isolation of highly polarized molecules, in aqueous solution ready for use in in vivo MRI diagnostic imaging, by means of phase transfer.

More particularly, in one embodiment, the present invention relates to a procedure for the preparation of aqueous solutions of hyperpolarized molecules in which, in a single step, the said hyperpolarized molecules is separated from the crude organic solution by means of a fast phase-transfer extraction and thus isolated in an impurity-free aqueous solution, ready for use in the MRI diagnostic imaging of organs, regions or tissues of the human or animal body.

Advantageously, by using the process of the invention the hyperpolarization product is obtained, at one time, totally free from the organic solvent, unreacted substrate and hydrogenation catalyst impurities, in an aqueous solution ready for use in in vivo MRI application without requiring any further purification and/or subsequent formulation.

Preferably, in the process of the present invention the hyperpolarized molecule (or MR imaging agent) is obtained by addition of para-hydrogen to a suitable unsaturated substrate (or "MR agent precursor", or, simply, "precursor" as used herein interchangeably) that is soluble in an organic solvent.

According to the present invention, and unless otherwise indicated, the term "MR agent" or "MR imaging agent", as used herein interchangeably, refers to a substance or a molecule containing at least one, proton or non-proton, hyperpolarized nucleus able to produce a magnetic resonance signal.

Organic solvents suitable for the purpose of the invention are immiscible with water and, preferably, comprise organochlorinated solvents such as, for example, chloroform, dichloromethane, carbon tetrachloride, aromatic solvents such as, for instance, benzene and toluene, ethers such as, for instance, diethylether, diisopropylether and butylether, aliphatic hydrocarbons such as, for instance, pentane, hexane, heptane, octane and cyclohexane, ethyl acetate and long chain alcohols such as, for example, butanol, pentanol, hexanol, and so on. Among them, preferred are chlorinated solvents and the above hydrocarbons, wherein particularly preferred are chloroform and dichloromethane.

The hydrogenation reaction is preferably performed by use of a PHIP technique, in the presence of a hydrogenation catalyst, that is suitably selected so as to be soluble in organic solvents but insoluble in water and aqueous solvents. Typically, the above catalyst is used in catalytic amounts known to a skilled person, for instance in a substrate/catalyst ratio ranging from 10:1 to 5:1. Examples of catalysts suitable for the use of the present invention include rhodium complexes of formula [Rh(diphosphine)diene)]$^+$[anion]$^-$, where the diphosphine is preferably selected from DPPB (1,4-Bis(diphenylphosphino)butane), DPPE (1,2-Bis(diphenylphosphino)ethane) and derivatives thereof including, for instance, the chiral phosphines such as DINAP (2,2'-Bis(diphenylphosphino)-1,1'-binaftyl), CHIRAPHOS (2,3-diphenylphosphinobutane), DIOP (1,4-Bis(diphenylphosphino)-1,4-bisdeoxy-2,3-O-isopropyliden-L-treitol), and DIP AMP (1,2-Bis[(2-methoxyphenyl)(phenilphosphino)]ethane); the diene is preferably selected from 1,5-cyclooctadiene and norbornadiene, and the anion can be any anion, but, preferably, tetrafluoroborate or trifluoromethyl sulfonate. Among them, preferred are the catalysts in which the phosphine group is diphenylphosphinobutane, while the [Bis(diphenylphosphinobutane)(1,5-cyclooctadiene)]Rh(I) is particularly preferred.

MR agent precursors suitable for the use of the instant invention comprise hydrogenatable substrates, typically including one or more unsaturated bonds, e.g. double or triple carbon-carbon bonds, that are well soluble in organic solvents and less soluble (i.e. poorly soluble) or, preferably, completely insoluble in water and able to generate corresponding parahydrogenated molecules that, conversely, present an increased water solubility, or, alternatively, that are rapidly and selectively converted into water-soluble molecules, preferably by the action of the sole water or of an appropriate aqueous solvent.

According to the present invention, and unless otherwise indicated, the expression "poorly water soluble" or "scarcely water soluble", as used herein interchangeably with reference to a MR agent precursors according to the invention, refers to a compound that has a minimal solubility in water, preferably less than 20%, more preferably, less than 5% and, even most preferably, less than 1% of the of the total precursor amount.

Advantageously, the above conditions make possible to operate the hydrogenation reaction in an organic solvent immiscible with water, and to separate the hyperpolarized product, or a water soluble derivative thereof, in an aqueous phase, by simple dilution of the crude reaction mixture with water, or with a suitable aqueous solution, essentially as shown in FIG. 1 and FIG. 4, respectively.

It goes without saying that, for in vivo applications, the unsaturated substrate must result into a hyperpolarized product that is physiologically acceptable as such, or that is isolable from the crude reaction in the form of a physiologically tolerable derivative thereof.

In a preferred embodiment, the instant invention relates to a process in which a suitable unsaturated substrate is solubilised in an organic solvent immiscible with water and hydrogenated with para-hydrogen, in the presence of a catalyst soluble in the organic solvent but insoluble in water and, more generally, in aqueous solvents, to give the corresponding para-hydrogenated compound that is quickly extracted from the organic reaction medium (crude solution) simply by diluting this latter with water, or with an appropriate aqueous solution, and then collecting the aqueous phase containing the hyperpolarized product.

In an alternative embodiment, the instant invention relates to a process in which a suitable unsaturated precursor is solubilised in an organic solvent immiscible with water and hydrogenated with para-hydrogen, in the presence of a catalyst soluble in the organic solvent but insoluble in water and, more generally, in aqueous solvents, to give the corresponding para-hydrogenated compound; this last is quickly and selectively converted into a water soluble derivative thereof that is extracted from the organic reaction medium simply by diluting it with water or a suitable aqueous solution and then collecting the aqueous phase containing the hyperpolarized derivative compound.

More particularly, in a preferred embodiment the instant invention relates to a process for preparing aqueous solutions of hyperpolarized molecules wherein:

a) a suitable unsaturated substrate is solubilised in an organic solvent immiscible with water and hydrogenated with para-hydrogen, in the presence of a catalyst soluble in the organic solvent but insoluble in water to give the corresponding para-hydrogenated compound, and b) the para-hydrogenated compound is isolated (as such) from the organic reaction medium by diluting this latter with water, or with an aqueous solvent, and then collecting the aqueous phase containing the hyperpolarized product; or alternatively, c) the para-hydrogenated molecule obtained at step a) is quickly and selectively converted into a water soluble derivative thereof that is isolated from the organic reaction medium by diluting this latter with water, or with a suitable aqueous solution, and then collecting the aqueous phase containing the hyperpolarized derivative compound.

In a preferred embodiment of the invention, the para-hydrogenated molecule obtained according to step a) of the above process is rapidly and selectively converted into a water soluble derivative thereof simply by effect of the dilution of the organic reaction medium with water or with a suitable aqueous solution, and is then easily isolated by the crude reaction by collecting the aqueous phase in which it is comprised.

Accordingly, in a particularly preferred embodiment the instant invention relates to a process wherein:

a) a suitable unsaturated substrate is solubilised in an organic solvent immiscible with water and hydrogenated with para-hydrogen, in the presence of a catalyst soluble into the organic solvent but water insoluble to give the corresponding para-hydrogenated compound, and c') the para-hydrogenated molecule obtained at step a) is rapidly and selectively converted into a water soluble derivative thereof by diluting the crude organic solution with water, or with a suitable aqueous solution, that is then isolated by collecting the aqueous phase in which it is comprised.

According to the present invention, and unless otherwise indicated, the term "aqueous solution" or "suitable aqueous solution", herein used interchangeably, refers to a sterile water or saline solution, optionally properly buffered, in any case physiologically tolerable and usable in in vivo diagnostic applications, or, moreover, an aqueous solution as defined above, further including a suitable amount of a properly selected reagent capable of promoting the rapid and selective conversion of the hyperpolarized molecule into a water soluble derivative and to generate, as a result, a physiologically acceptable aqueous solution of the same, suitable for use in in vivo diagnostic imaging without further purification.

In this regard, it is clear from the foregoing that, when the reagent used for promoting the said conversion is not itself physiologically acceptable, its quantity in the added aqueous solution must be precisely determined, based on the stoichiometry of the reaction itself, so as to be completely used in the conversion reaction of the parahydrogenated molecule to a water soluble and physiologically compatible (at physiological pH condition) derivative thereof, and to generate a physiologically acceptable aqueous solution of the same, ready for use in in vivo diagnostic MRI imaging.

Suitable examples of aqueous solution according to the instant invention comprise water, a physiological saline solution, an aqueous solution containing the minimum amount of a base, e.g. NaOH, or of an acid such as citric acid or acetic acid, capable of promoting the hydrolysis of a suitable parahydrogenated substrate, or an aqueous solution comprising a physiologically acceptable reagent such as, for example, an amine or an amino acid (e.g. glycine, leucine, alanine, serine), allowing to promote the para-hydrogenated substrate aminolysis, to give a water soluble and physiologically compatible derivative thereof, for instance in the form of a physiologically acceptable salt, e.g. of an acid, or of an amide physiologically acceptable.

Particularly preferred for the scope of the instant invention are water, physiological saline solutions, water solutions of NaOH, and water solutions of citric or acetic acid.

In a preferred embodiment of the invention, the volume of aqueous solution added to the organic reaction medium is equal to the volume of organic solvent used for solubilising the unsaturated substrate and the hydrogenation catalyst. More preferably the aqueous solution is used in a suitable amount so as to provide an aqueous solution of the hyperpolarized molecule of interest ready for use without need of further concentration. In case, conversely, a suitable dilution of the collected aqueous phase containing the hyperpolarized compound may, optionally, be done by using a suitable amount of sterile water or saline solution.

MR agent precursors suitable for the use of the instant invention comprise hydrogenatable substrates, typically including one or more unsaturated bonds.

In general, the MR agent precursor for the use of the instant invention should be highly polarisable.

Preferred precursor agents are polarisable to a degree corresponding to at least 5%, preferably at least 10% and, more preferably of at least 30% or even higher, and the hyperpolarized molecule they provide is capable to maintain the polarisation for a period of time sufficient to allow the imaging procedure.

Preferred precursor agents according to the invention should, moreover, have a low molecular weight, preferably less than 500 D, and, more preferably from 100 to 300 D.

Importantly, and as formerly said, the substrate molecule for the use of the invention are well soluble in an organic phase and less soluble or insoluble in an aqueous phase and able to generate a corresponding parahydrogenated molecule that is, conversely, better soluble in water, or, alternatively, that is rapidly and selectively converted into water-soluble molecules, by means of an appropriate chemical reaction and, preferably, by the sole action of water or of an appropriate aqueous solution.

Suitable examples, for instance, include substituted alkynes that, for partial saturation with para-hydrogen, generate the corresponding substituted alkenes. Preferably, the difference in water solubility between starting alkynes and corresponding alkenes produced with the para-hydrogenation is at least 60% in favour of the obtained alkene that has to be characterized by a higher water solubility.

A further class of useful substrates includes substituted alkenes that by hydrogenation with para-hydrogen provide the corresponding substituted alkanes, with a difference in the water solubility of at least 60% in favour of the saturated hydrogenation product, the alkane, that has to be characterized by the higher solubility in the aqueous phase.

Examples of precursors that after para-hydrogenation can be rapidly and easily be converted into a water soluble derivative include carboxylic acid anhydrides, activated esters and ketenes.

A sufficiently stable unsaturated anhydride can, in fact, be para-hydrogenated in an organic solvent and then hydrolyzed (by dilution of the reaction medium) with a basic aqueous solution to form the corresponding carboxylic acid which, preferably, passes into the aqueous solution, optionally in the form of a physiologically acceptable salt, and can be then isolated by simple separation of the aqueous phase itself. The exact amount of the base to be comprised in the aqueous solution (added to the organic phase) is preferably calculated so as to generate, after extraction of the derivative, e.g. the carboxylic acid, an aqueous solution thereof having a physiological pH, ready for in vivo diagnostic by MRI.

As already explained, suitable precursors for the use of the instant invention all contain, necessarily, at least one unsaturation site, for instance a double or a triple C—C bond, which is reduced by addition of para-hydrogen to give the corresponding parahydrogenated compound.

However, for the formerly explained reasons, in in vivo magnetic resonance imaging the use of molecules hyperpolarized at a non-proton nucleus (or heteronucleus) is certainly to be considered as preferable.

In a particularly preferred embodiment thereof, the instant invention relates to a procedure for the preparation of aqueous solutions of hyperpolarized molecules (or MR imaging agents) that comprise an hyperpolarized non-proton nucleus (or heteronucleus, as used herein interchangeably), for instance a $^{19}F$, $^{13}C$, $^{15}N$ or $^{29}Si$ nucleus and, especially, a $^{13}C$ or a $^{15}N$ hyperpolarized nucleus.

In general, the hetero-nuclear hyperpolarization by use of a PHIP procedure, as per the case of the present invention, is obtained by transferring the polarization from the protons of the para-hydrogen to the heteronucleus of interest.

In greater detail, in order to use a parahydrogenated compound as, for instance, $^{13}C$ MRI contrast agent it is necessary that the "anti-phase" signal of the hyperpolarized carbon atom, obtained through polarization transfer from the parahydrogen to the concerned carbon, is totally converted in an "in-phase" signal, useful for imaging acquisition. This step can be performed by using an appropriate pulse sequence as disclosed, for instance, in Goldman M., Johannesson H., C. R. Phisique 2005, 6, 575, or by applying an appropriate field cycling procedure to the parahydrogenated product. This last includes rapidly introducing (non-adiabatically) the hydrogenated sample into a magnetic screen (field intensity=0.1 μT), and then slowly removing (adiabatically) the screen to bring the sample to field values corresponding to the Earth's magnetic field (50 μT) (in this respect see, for instance, C. R. Phisique 2004, 5, 315).

In line with the above, and according to a preferred embodiment, the procedure of the instant invention comprises the application of an appropriate field cycling procedure to the parahydrogenated product, for instance obtained at the step a) of the former invention process, in order to promote the polarization transfer from the proton nuclei (deriving from the parahydrogen addition) to the non-proton nucleus of interest and to give the corresponding heteronuclear hyperpolarized molecule that is then extracted from the crude organic solution by phase transfer and isolated in the aqueous phase according to steps b) c) or c') of the said former processes.

More specifically, in an especially preferred embodiment, the instant invention relates to a process wherein:

a) a suitable unsaturated substrate is solubilised in an organic solvent immiscible with water and hydrogenated with para-hydrogen, in the presence of a catalyst soluble into the organic solvent but water insoluble to give the corresponding para-hydrogenated compound, a') an appropriate field cycling procedure is applied, and b) the heteronuclear hyperpolarized molecule thus obtained is isolated as such from the organic reaction medium by diluting it with water, or with an aqueous solvent, and then collecting the aqueous phase containing the hyperpolarized product; or alternatively, c) the hyperpolarized molecule obtained according to step a') is quickly and selectively converted into a water soluble derivative thereof that is isolated from the crude solution by diluting this last with water, or with a suitable aqueous solution, and then collecting the aqueous phase in which the heteronuclear hyperpolarized derivative of interest is comprised.

Substrate compounds useful for preparing aqueous solutions of heteronuclear hyperpolarized molecules according to a preferred embodiment of the instant invention include, together with an unsaturated bond, a non proton nucleus having nuclear spin=½ such as, for instance, $^{13}C$, $^{15}N$, $^{29}Si$ and $^{19}F$ that may be present in its naturally occurring isotopic abundance or, preferably, is purportedly enriched in the substrate molecule that becomes, therefore, enriched or "labelled" in the said non-proton nucleus.

For in vivo applications, preferred substrate compounds according to the invention are $^{15}N$ or $^{13}C$ and, especially, $^{13}C$ enriched and have a $^{13}C$ enrichment degree of at least 10% or more, preferably 50% or more, especially preferably 99% or even greater.

Particularly preferred are substrates including a carbon atom, preferably $^{13}C$ enriched, within a distance of three bonds from the proton added to the molecule with para-hydrogen and endowed with a long $T_1$ relaxation time.

Carbon atoms that meet these requirements for instance include carbon atoms of carbonyl groups or quaternary carbon atoms. In this case, in fact, the scalar coupling between the protons added with parahydrogenation and the $^{13}C$ labelled suitable carbonyl group (or quaternary carbon compound) makes the transfer of the polarization to the said heteronucleus possible, whereas its long relaxation time allows to maintain the polarization for some tens of seconds, and even more preferably for more than 60 seconds, under physiological conditions.

Accordingly, elected substrates for the use of the invention comprise an alkenyl or alkynyl group and one $^{13}C$-enriched carbonyl substituent.

Suitable examples of substrates of this type comprise the anhydrides of carboxylic acids which include in their molecular structure a suitable unsaturation.

Preferred anhydrides according to the instant invention include at least one unsaturation site and can be internal or not, mixed, that is to say of formula $R_1$—COOCO—$R_2$, where $R_1$ is different from $R_2$, or symmetric, i.e. of formula R—COOOC—R. The mixed anhydrides, in turn, may be formed by two unsaturated carboxylic acid or by an unsaturated acid and one saturated.

In the first case, the hydrogenation reaction will provide two acids $R_1$—COOH and $R_2$—COOH, both polarized, while, in the second case, the hydrogenation reaction will provide only one polarized acid, for instance $R_1$—COOH, and a non polarized "by-product", for instance $R_2$—COOH. In this latter case, however, the use of an appropriate pulse sequence may be exploited to transfer the polarization from the carbonyl group adjacent to the unsaturation, in $R_1$, to the second carbonyl group.

The use of this procedure, for instance schematized in FIG. 5, makes thus possible to polarize, through an "indirect" polarization procedure, a carboxylic acid without unsaturation and, thus, not directly hydrogenable (i.e., for instance, the former $R_2$—COOH residue).

Especially preferred for the use of the instant invention are maleic, crotonic and cis-butenoic (also known as isocrotonic)

anhydrides, and the corresponding mixed anhydrides, such as the cis-butenoic-acetic and the cis-butenoic-ethyl carboxylic anhydrides.

A second class of substrate compounds according to the invention that are soluble in organic solvent, and that, after hydrogenation, can be quickly converted into water-soluble derivatives is represented by activated esters.

Illustrative examples include:

1) silyl esters such as, for instance, trialkyl silyl esters of formula R—COO—SiR$_3$, aryl-dialkyl silyl esters of formula R—COO—SiArR$_2$, bisaryl-alkyl silyl esters of formula R—COO—SiAr$_2$R and the tris-aryl silyl esters of formula R—COO—SiAr$_3$. These compounds can, in fact, be hydrogenated in an organic solvent and then hydrolyzed to the corresponding carboxylic acids (RCOOH) with a weakly acidic aqueous solution: the so obtained carboxylic acid pass directly into the aqueous phase and are easily isolated by separation of this latter.
2) Stannyl esters: for instance, a suitable hydrolysis of the water insoluble tris-alkyl stannyl esters of formula R—COO—SnR$_3$ may be performed, after the hydrogenation step, by reaction with fluorides.
3) Acyl-oxy alkyl esters: for instance esters of general formula R—COO—CHR'OCOR", where R' is H or Me, and R" is Me or t-Bu can be easily hydrolyzed by reaction with either acidic or basic solutions or, even, in the presence of a suitable enzymatic catalyst.
4) Isoprenylated esters: these esters decompose by thermolysis according to the following scheme:

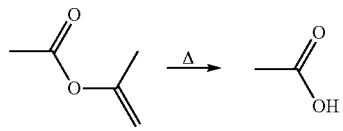

5) tertiary-alkyl esters of formula R—COO—CR'$_3$ where R' is Ph or Me, wherein the hydrolysis may be sped, for instance by use of super acid resins.

A further class of unsaturated substrates according to the invention are ketenes. Indeed, given the tension ring, they can be easily hydrogenated with para-hydrogen, and thereafter, again because of the tension, can be rapidly hydrolyzed to acids according to the scheme below:

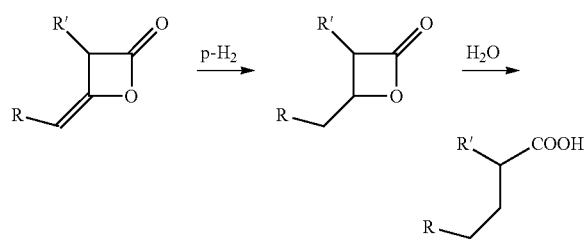

Then, the polarization can be suitably transferred to a heteronucleus of interest, for instance to the carbon atom of the carboxyl group formed with hydrolysis, where the coupling constant between this last and protons arising from para-hydrogen is large enough, or a suitable carbon atom or nitrogen present in R, preferably $^{13}$C or $^{15}$N enriched.

Especially preferred substrate compounds according to the instant invention include precursor of biomolecules of diagnostic interest that after hydrogenation, hyperpolarization transfer to a suitable heteronucleus and subsequent, optional, hydrolysis (or different appropriate chemical modification) rapidly and selectively provide a water soluble biomolecule of medical/diagnostic interest.

Substrate compounds of this type include, for instance, amino acids, neurotransmitters and, in general, metabolite precursors. Suitable examples, for instance, include maleic anhydride or maleic/fumaric esters that, after hydrogenation and hydrolysis will provide succinic acid, that finds advantageous use in the citric acid cycle diagnostic evaluation.

Additional examples include crotonic and/or isocrotonic anhydrides and esters, which by hydrogenation and hydrolysis afford butyric acid, which is a $C_4$ acid usually produced by microbial fermentation of carbohydrates and proteins in the large intestine of all animal species and seems to have diverse effects on cellular proliferation, apoptosis and differentiation that may be either pro-neoplastic or anti-neoplastic, depending upon factors such as the level of exposure, availability of other metabolic substrate, and the intracellular milieu.

Suitable β-γ unsaturated carboxylic acid derivatives may provide, after hydrogenation, suitable amino acids, for instance glutamic acid, preferably $^{13}$C enriched at the carboxyl atom, that may be used for evaluation of the glutamate metabolism (synthesis of the inhibitory GABA in GABA-ergic neurons catalyzed by glutamate decarboxylase (GAD); disposal of excess or waste nitrogen by glutamate deamination, catalysed by glutamate dehydrogenase) and of glutamate transporters in neuronal and glial membranes.

On the other side, the possible use of unsaturated substrates suitably modified, for instance by introduction of an appropriate functional group which suitably increases (or decreases) their solubility in aqueous solvent has to be considered as comprised within the scope of the present invention. For instance, a functional group such as a benzyloxy group can be used to increase the solubility of the substrate compound in an organic solvent, and, then, it may be removed, for instance by hydrogenolysis, during the para-hydrogenation reaction, to give a hydrogenated compound endowed with increased water solubility.

Substrate compounds modified accordingly constitute a further aspect of the instant invention.

Substrate compounds according to the invention, i.e. the unsaturated substrates for parahydrogenation, preferably labelled with $^{13}$C, $^{15}$N or other heteronuclei with nuclear spin ½, are well known and commercially available or, they can readily be prepared according to known methods.

Similarly, the catalysts used in the process in question are known or, if not commercially available as such, are prepared with known methods. Similarly, the appropriate organic solvent immiscible with water can be chosen from those listed above, readily available on the market. Optionally, the system solvent may also be constituted by an appropriate mixture of solvents.

The impurity-free aqueous solution of a hyperpolarized molecule obtained by using the process of the instant invention are stable for a clinically acceptable period of time.

Aqueous solutions according to the instant invention preferably include the hyperpolarized molecule in a concentration ranging between 0.002 and 1.0 M and preferably between 0.01 and 0.5 M.

The impurity-free aqueous solution of a hyperpolarized molecule obtained by using the process of the instant invention find advantageous use in in vitro, ex vivo and, especially, in vivo MR diagnostic imaging of a human or animal body organ, fluid, region or tissue, as well as for the diagnostic assessment of physiological parameters of diagnostic interest.

For instance, maleic acid, whose carboxyl $^{13}$C chemical shift is pH-dependent in the range 6.0÷7.0, is attainable by hydrogenation and hydrolysis of acetylenedicarboxylic esters, and may find application as probe for the pH evaluation in tissues.

In addition, aqueous solutions of a hyperpolarized molecule of biological interest obtained by using the process of the instant invention may find advantageous use in the emerging field concerning the evaluation of metabolic profiles of diagnostic interest by use of MR imaging techniques.

The aqueous solutions of hyperpolarized molecules of the invention have a wide range of applications as they can be used for intravasal, (for instance intravenous, intraarterial, intracoronaric, intraventricular administration and the like), intrathecal, intraperitoneal, intralymphatic and intracavital administrations. The solutions or suspensions of the compounds of this invention can also be formulated as aerosol to be used in aerosol-bronchography and instillation.

As formerly said, the impurity-free aqueous solution of a hyperpolarized molecule obtained by using the process of the instant invention are usable as such in the in vivo MRI diagnostic imaging, without need of further purification. and/or formulation.

Accordingly, in an additional embodiment, the instant invention relates to a MR contrast agent comprising an impurity-free aqueous solution of a hyperpolarized molecule obtained by using a process according to the instant invention.

In a different embodiment the invention relates to the use of the aqueous solution of hyperpolarized molecules according to the invention for the preparation of an MR imaging agent for use in the diagnostic evaluation of a human or animal body organ, tissues or region or for the assessment of a biological data or metabolic evaluations by means of MR imaging techniques.

In a still further embodiment, the invention relates to an aqueous solution of an hyperpolarized molecule obtained with the process of the instant invention for use in a method of diagnostic imaging in which MR images of a human or animal body organ, region or tissues or biological parameter assessment or metabolic profile evaluations are obtained by use of MR imaging techniques.

More particularly, viewed from a still different view, the instant invention relates to a method for the diagnostic visualization of a human or animal body organ, region, fluid or tissue by means of Magnetic Resonance Imaging, the said method comprising:

i) parahydrogenating a MR imaging agent precursor in an organic solvent immiscible with water and in the presence of a catalyst soluble into the organic solvent but insoluble into water by use of PHIP technique, optionally applying a suitable field cycling to give the corresponding MR agent with a net hyperpolarization on a non-proton nucleus, diluting the organic reaction medium with water or a suitable aqueous solution and collecting the aqueous phase containing the hyperpolarized MR agent, ii) administering the said aqueous phase to a human or animal body, iii) exposing the said human or animal body to a radiation frequency allowing to excite the hyperpolarized nucleus in the said MR agent, iv) recording the signal generated by the excited nucleus and generating an image of the body region or the biological data of interest from the said signal.

EXPERIMENTAL SECTION

EXPERIMENTAL RESULTS

With the aim to better illustrate the process object of the present invention the following examples are provided that are not intended to in any way limit the scope of the invention.

Example 1

Hyperpolarization Test

The symmetrical alkyne A, whose formula is reported below, was synthesized by transesterification of the acetylene bis-carboxylic acid bismethyl ester with diethyleneglycol monomethyl ether, in the presence of H$_2$SO$_4$ as catalyst. The (oligo)oxyethylenic chains have been suitably selected to preferably increase the water solubility of the parahydrogenated product B. In fact, the solubility in water of B is higher than that of the alkyne A.

The unsaturated substrate A was parahydrogenated in a 5 mm NMR tube equipped with a Young valve charged with acetone-d$_6$ (0.4 mL), [Bis(diphenylphosphino)butane](1,5-cyclooctadiene)rhodium(I) tetrafluoroborate as catalyst, (5 mg), previously activated with H$_2$, substrate A (0.02 mmol) and 4 atm of para-H$_2$ (52% enriched). The reaction was started by shaking the tube for 10 seconds (yield=85%) and the $^{13}$C signal recorded immediately after parahydrogenation was 1500 times enhanced.

Figure 1:
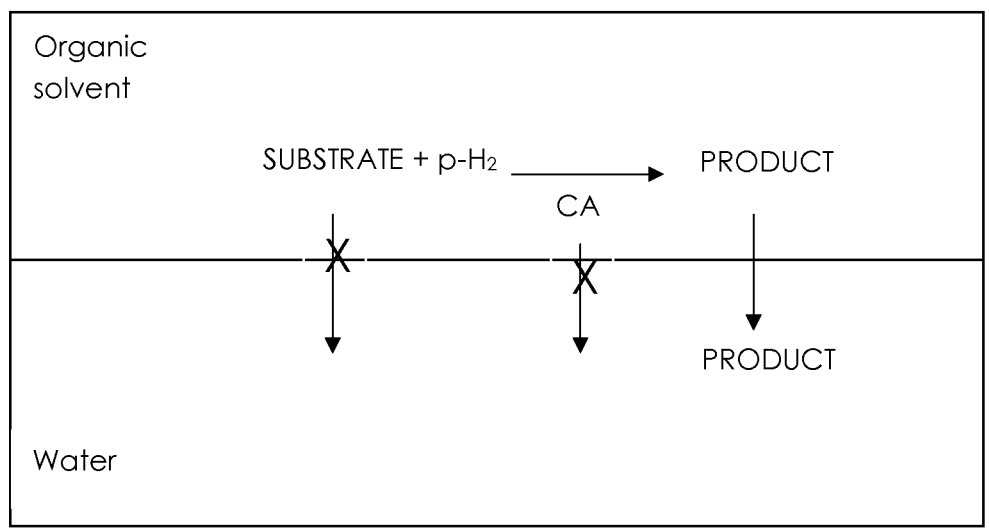
FIG. 1 shows a schematic presentation of the invention procedure for extracting and isolating the para-hydrogenated product by phase transfer
Figure 2:
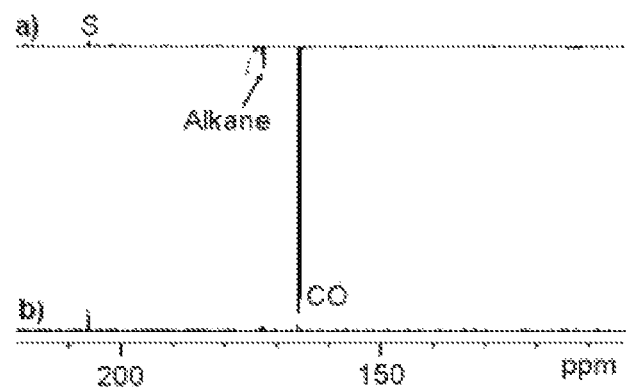
FIG. 2 shows $^{13}$C-NMR spectra (14 T, 298 K, acetone-d$_6$), of B ($^{13}$C-enriched) obtained by para-hydrogenation of A. a) spectrum recorded immediately after para-hydrogenation and field cycling; b) spectrum recorded after relaxation (5 minutes). In the provided spectrum S indicates the solvent and i denotes an impurity.

For the acquisition of an in phase $^{13}$C resonance, a magnetic field cycling was applied, as per U.S. Pat. No. 6,574,495 disclosure, to the hydrogenated sample: this was pursued by quickly inserting the tube into a μ-metal shield (field strength 0.1 μT), and then slowly removing the shield. The entire field cycling procedure took three to five seconds. The sample was then inserted into the spectrometer (14 T) and the high resolution NMR spectrum was acquired (shown in FIG. 2) showing a $^{13}C$ signal enhancement of about 250 times.

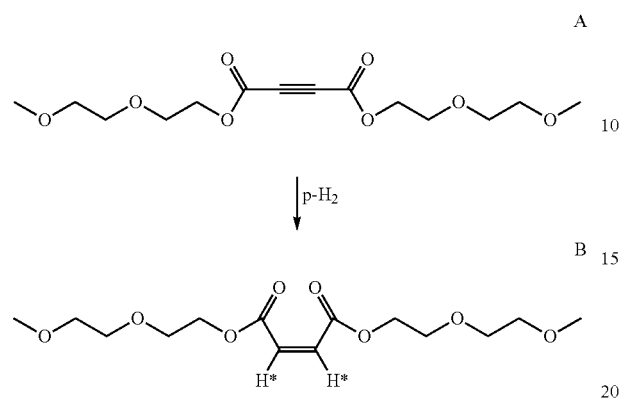

Example 2

Catalyst and Organic Solvent-free Aqueous Solution of the Hyperpolarized Compound of Example 1 by Phase Transfer A test confirming the process of the invention ability to provide a catalyst and organic solvent-free aqueous solution of a desired parahydrogenated molecule has been performed by using a solution of the above parahydrogenated compound B obtained by para-hydrogenating the corresponding compound A in $CDCl_3$/acetone-$d_6$ (6:1), under the same hydrogenation conditions used in pure acetone, and disclosed in example 1.

Figure 3:
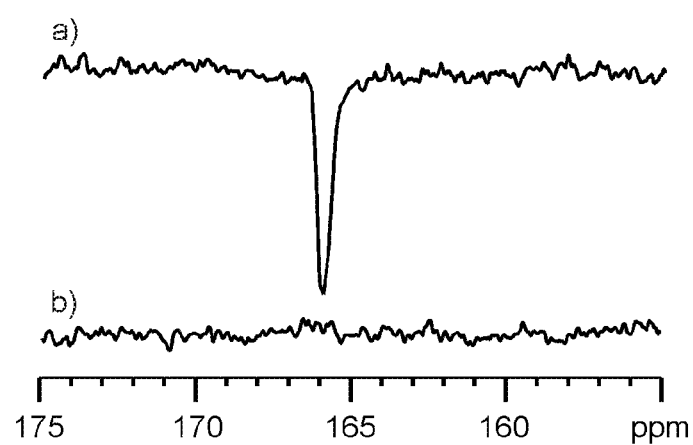
FIG. 3 shows $^{13}$C-NMR spectra (14 T, 298 K, D$_2$O) of B ($^{13}$C-enriched) obtained by para-hydrogenation of A. a) spectrum recorded immediately after para-hydrogenation, field cycling and extraction in water (D$_2$O) and b) spectrum recorded after relaxation (5 minutes).
Figure 4:
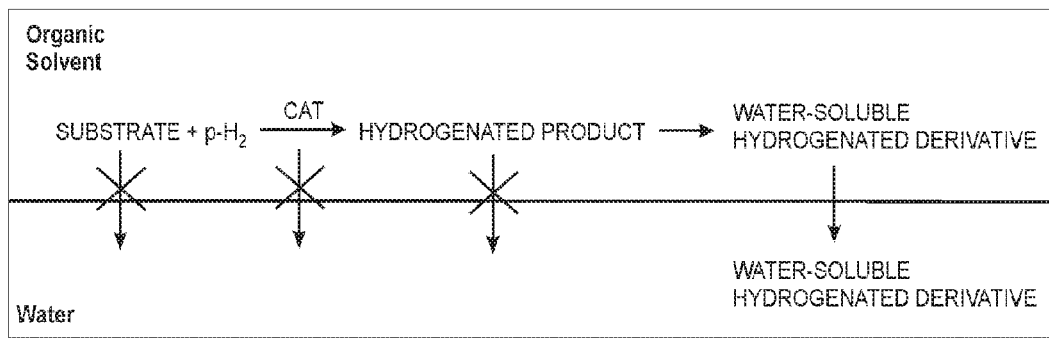
FIG. 4 shows a schematic presentation of the invention procedure for extracting and isolating the para-hydrogenation product by phase transfer, comprising firstly transforming it in a water soluble derivative.
Figure 5:
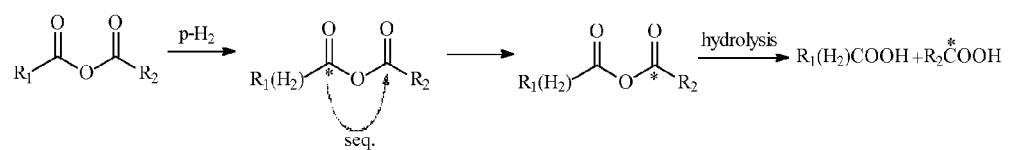
FIG. 5 shows an example of acid hyperpolarization obtained by transfer of polarization from a carbonyl to another in a mixed anhydride and further hydrolysis.

After the field cycling application, the tube was quickly opened and 0.4 mL of degassed $D_2O$ were added; the tube was shaken vigorously for three seconds and then let stand for five seconds, during which phase separation occurred. The water solution was taken by a syringe and transferred into a tube for NMR acquisition. A $^{13}C$ spectrum was acquired, reported in FIG. 3, showing a $^{13}C$ signal enhancement of 100 times. The signal enhancement obtained is lower than that obtained in pure acetone, probably because of a partial polarization loss due to relaxation during the entire process. Residual polarization is anyway sufficient for detection of an enhanced signal t 165.99 ppm, corresponding to B dissolved in $D_2O$. The quantity of B transferred into the water phase was estimated to be about 10% of the total.

Example 3

Aqueous Solution of Succinic Acid

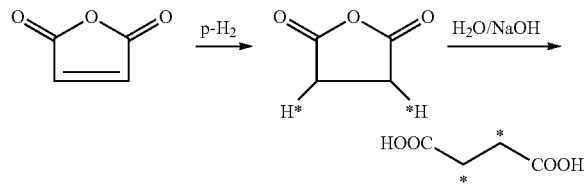

Maleic anhydride has been para-hydrogenated in a 6:1 $CDCl_3$/acetone-$d^6$ mixture (0.4 ml), in the presence of 5 mg of [Bis(diphenylphosphinobutane)(1,5-cyclooctadiene)]Rh (I) tetrafluoroborate (activated by reaction with $H_2$) and 5.5 atm of para-$H_2$ (52%). After 10 seconds of reaction the field cycling has been applied and 0.4 ml of 0.25 M NaOH in $D_2O$ have been added. The just formed succinic anhydride has therefore been converted to succinic acid. The tube was vigorously shaken and then let stand for 5 seconds. The water phase, containing succinic acid, has been transferred into a second tube for NMR acquisition.

Figure 6:
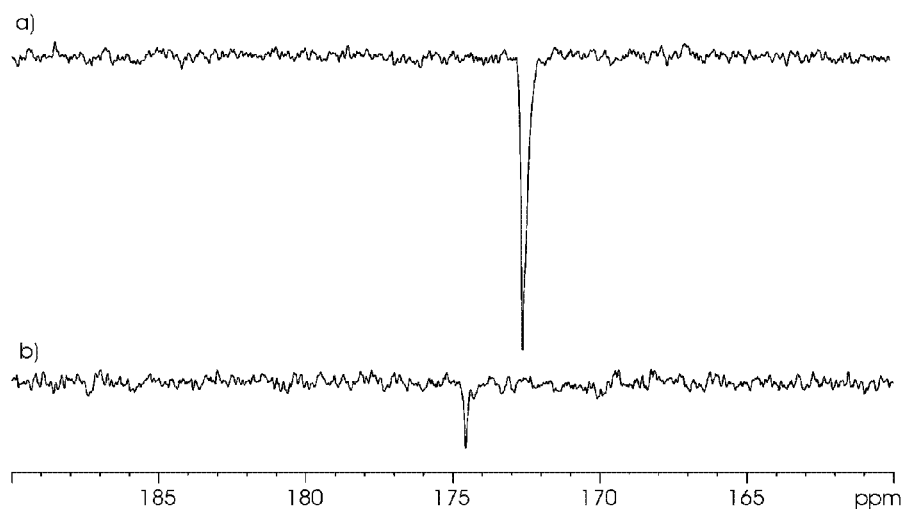
FIG. 6 shows $^{13}$C-NMR spectra (14 T, 298K) a) of succinic anhydride obtained by para-hydrogenation of maleic anhydride in CDCl$_3$ (spectrum recorded immediately after para-hydrogenation and field cycling); b) spectrum of the water solution containing succinic acid obtained after para-hydrogenation of maleic anhydride in CDCl$_3$, field cycling and hydrolysis of the succinic anhydride by NaOD in D$_2$O.

The resulting spectrum is reported in FIG. 6b: residual polarization after phase extraction allows the detection of an enhanced emission signal for succinic acid at 174.65 ppm (signal enhancement of about 30 times). All the succinic acid was transferred to the water phase and the final pH was neutral.

The low intensity of the observed signal, in spite of the high concentration of the final aqueous solution (about 0.12M) is due to the use of not $^{13}C$ enriched maleic anhydride.

Example 4

Use of an Activated Ester

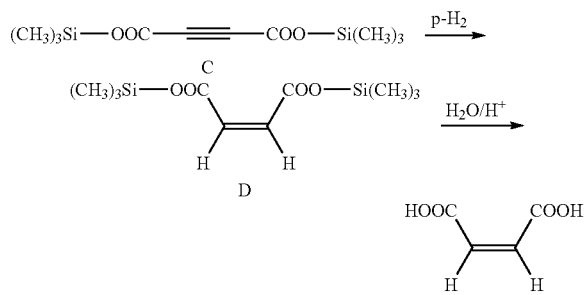

Figure 7:
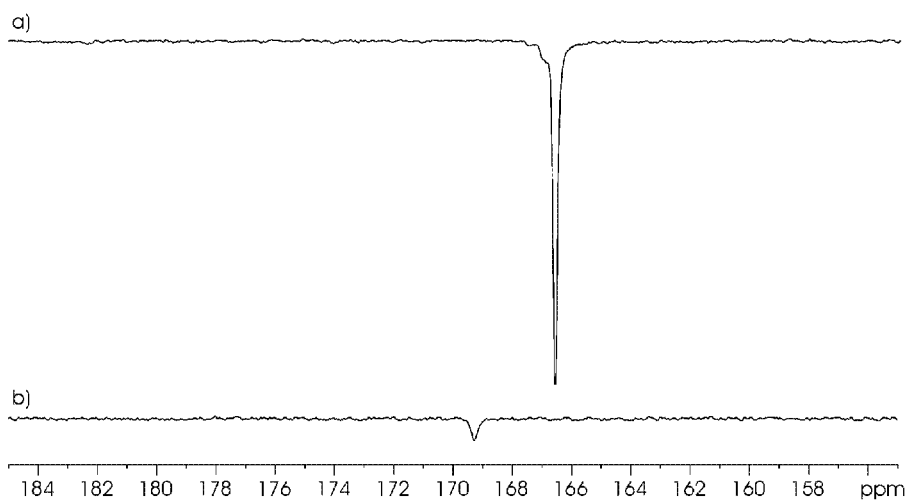
FIG. 7 shows $^{13}$C-NMR spectra (14 T, 298 K, acetone-d$_6$) of a) the alkene D (of example 4) obtained by para-hydrogenation of the acetylene bis-carboxylic acid trimethylsilyl ester C in acetone-d$_6$ (spectrum recorded immediately after para-hydrogenation and field cycling) and b) of the maleic acid obtained by parahydrogenation of C in acetone-d$_6$ and subsequent hydrolysis with acetic acid solution in D$_2$O (spectrum recorded on the obtained mixture acetone-d$_6$/D$_2$O).

The reaction has been carried out by using acetylene bis-carboxylic acid trimethylsilyl ester (C) as unsaturated substrate compound that, after hydrogenation with para-hydrogen results in the corresponding alkene (D) in its turn converted into the corresponding maleic acid by using a weakly acidic aqueous solution. FIG. 7 shows $^{13}C$-NMR spectra (14 T, 298 K, acetone-$d_6$) of the alkene D obtained a) immediately after para-hydrogenation and field cycling and b) after the subsequent hydrolysis with acetic acid solution in $D_2O$. The obtained results demonstrate the very high signal enhancement recovered (about 700 times) with hyperpolarization, and confirm that a polarization is still observable after hydrolysis.

The invention claimed is:
1. A one-step process for the preparation of an aqueous solution of hyperpolarized molecules that comprises para-hydrogenating a suitable unsaturated substrate in an organic solvent immiscible with water and in the presence of a catalyst soluble in the organic solvent but insoluble in water and isolating the hyperpolarized molecule through a phase transfer extraction, by diluting the crude reaction medium with an aqueous solution and collecting the aqueous phase containing the hyperpolarized molecule ready for use in vivo MRI applications.
2. A process according to claim 1 wherein the unsaturated substrate is insoluble or scarcely water soluble and the corresponding hyperpolarized molecule is water soluble.
3. A process according to claim 2 wherein the unsaturated substrate comprises a suitable alkynyl or alkenyl group and the corresponding para-hydrogenated molecule comprises the corresponding alkenyl or saturated alkyl group, respectively.

4. A process according to claim 3 wherein the unsaturated substrate further comprises a hydrolysable group.

5. A process according to claim 1 wherein the organic solvent immiscible with water is selected from an organochlorinated solvent, an aromatic or etheral solvent, or an aliphatic hydrocarbon, ethyl acetate or a long chain alcohol.

6. A process according to claim 1 wherein the unsaturated substrate is labelled with a non-proton nucleus having nuclear spin ½.

7. A process according to claim 6 wherein the unsaturated substrate is $^{13}C$ or $^{15}N$ enriched.

8. A process according to claim 1 wherein the catalyst is [Bis(diphenylphosphinobutane)(1,5-cyclooctadiene)]Rh(I).

9. A process according to claim 1 wherein:
a) a suitable unsaturated substrate is solubilised in an organic solvent immiscible with water and hydrogenated with para-hydrogen, in the presence of a catalyst soluble in the organic solvent but insoluble in water, to give the corresponding para-hydrogenated compound, and
b) the para-hydrogenated compound is isolated from the organic reaction medium by diluting it with water, or with an aqueous solution, and then collecting the aqueous phase containing the hyperpolarized product; or alternatively,
c) the para-hydrogenated compound obtained in step a) is quickly and selectively converted into a water soluble derivative thereof that is isolated from the organic reaction medium by diluting it with water, or with an aqueous solution, and then collecting the aqueous phase containing the hyperpolarized derivative compound.

10. A process according to claim 9 wherein the para-hydrogenated molecule obtained in step a) is rapidly and selectively converted into a water soluble derivative thereof by diluting the organic reaction medium with water or an aqueous solution.

11. A process according to claim 9 in which, additionally, a suitable field cycling is applied to the parahydrogenated molecule obtained in the step a) of the process so as to give the corresponding molecule with a net polarization on a suitable heteronucleus.

12. A process according to claim 11 in which the heteronucleus is a $^{13}C$ or a $^{15}N$ enriched nucleus.

13. A MR contrast agent consisting of the aqueous phase collected from the process of any one of claim 1, 9 or 11.

14. A method for the diagnostic visualization of a human or animal body organ, region, fluid or tissue by use of Magnetic Resonance Imaging comprising:
i) parahydrogenating a MR imaging agent precursor in an organic solvent immiscible with water and in the presence of a catalyst soluble into the organic solvent but insoluble in water by use of the PHIP technique, optionally applying a suitable field cycling to give the corresponding MR agent with a net hyperpolarization on a non-proton nucleus, diluting the organic reaction medium with water or an aqueous solution and collecting, by means of a phase transfer extraction, the aqueous phase containing the hyperpolarized MR agent ready for use in in vivo MRI applications;
ii) administering the said aqueous phase to a human or animal body;
iii) exposing the said human or animal body to a radiation frequency allowing to excite the hyperpolarized nucleus in the said MR agent; and
iv) recording the signal generated by the excited nucleus and generating an image of the body region or the biological data of interest from the said signal.

* * * * *